United States Patent [19]

Huang

[11] Patent Number: 4,681,855
[45] Date of Patent: Jul. 21, 1987

[54] HUMIDITY SENSING AND MEASUREMENT EMPLOYING HALOGENATED ORGANIC POLYMER MEMBRANES

[75] Inventor: Peter H. Huang, Gaithersburg, Md.

[73] Assignee: The United States of America as represented by the Secretary of Commerce, Washington, D.C.

[21] Appl. No.: 762,740

[22] Filed: Aug. 5, 1985

[51] Int. Cl.⁴ ............................................. G01N 27/12
[52] U.S. Cl. .......................................... 436/39; 73/23; 338/35; 422/90; 422/91
[58] Field of Search .................. 73/23, 27 R; 338/34, 338/35; 204/426, 430; 422/83, 86, 88, 90, 91, 98; 436/39, 127

[56] References Cited

U.S. PATENT DOCUMENTS

| 4,003,707 | 1/1977 | Lubbers et al. | 436/172 |
| 4,083,765 | 4/1978 | Lawson | 204/430 X |
| 4,332,665 | 1/1982 | Kimoto et al. | 204/296 |
| 4,361,026 | 11/1982 | Muller et al. | 73/23 |
| 4,376,140 | 7/1983 | Kimoto et al. | 427/244 |
| 4,382,123 | 11/1983 | Kimoto et al. | 521/27 |
| 4,549,134 | 10/1985 | Weiss | 338/35 X |

OTHER PUBLICATIONS

Huang; Electrical and Thermodynamic Characterization of Water Vapor/Polymeric Film System for Humidity Sensing; Sensors & Actuators, 8(1985)23–28.

Hermans; CO, $CO_2$, $H_4$ and $H_2O$ Sensing by Polymer Covered Interdigitated Electrode Structures; Sensors & Actuators, 5(1984) 181–186.

Thoma et al; A Capacitance Humidity-Sensing Transducer; IEEE Transactions on Components, Hybreds, and Manufacturing Tech. CHMT 2 (3) 9/79 321–323.

Misevich; Capacitive Humidity Transducer IEEE Transactions on Industrial Electronics and Control Instrumentation IECI-16 (1) 7/69 6–12.

Randin, Polymeric Electrolyte for Electrooptical Device CA95(2):16047t, 1980.

Primary Examiner—Barry S. Richman
Assistant Examiner—Michael S. Gzybowski
Attorney, Agent, or Firm—Alvin J. Englert; Mitchell W. Shapiro

[57] ABSTRACT

Thin films of hygroscopic, halogenated organic polymer having pendant groups of a relatively strong acidic type (e.g., sulfonic groups) and pendant groups of a relatively weak acidic type (e.g., carboxylic groups) are employed for humidity sensing by electronic, acoustic, and optical techniques.

30 Claims, 4 Drawing Figures

HUMIDITY SENSING AND MEASUREMENT EMPLOYING HALOGENATED ORGANIC POLYMER MEMBRANES

BACKGROUND OF THE INVENTION

The present invention relates to methods and devices for sensing atmospheric humidity and is particularly concerned with the use of hygroscopic organic polymer membranes in such applications.

The use of organic polymers for humidity sensing is well known, and various devices incorporating organic polymer humidity sensing elements have been proposed in the prior art. Basically speaking, humidity sensing devices of the foregoing type operate by the detection of a physical property of the polymer which varies as a function of the water content of the polymer (i.e., which varies as water is adsorbed and desorbed with changing humidity conditions). Because the water content of the polymer is directly related to relative humidity at any given temperature, the value of the detected property at a particular temperature will provide a direct indication of relative humidity.

In perhaps the most common form of polymeric humidity sensor, an electrical property of the sensor is detected to determine humidity—most often resistance or conductance (the reciprocal of resistance), although capacitive type sensors are also known. Polymeric electronic humidity sensors are generally fabricated from a class of polymers known as polyelectrolytes or ion exchange resins. These materials are characterized by an insoluble polymer backbone with attached functional groups capable of exchanging one ion for another of similar type (e.g., cation for cation). The ion exchange capabilities of these materials are not actually utilized for humidity sensing. Rather, it is the characteristic change in properties of these materials as they adsorb and desorb water which is important. Exemplary functional groups of the cation exchange type include sulfonic, phenolic, phosphonic, and carboxylic acid groups. Conductivity among different polymers at a given temperature and water content will vary depending upon the particular functional group present, with the relatively strong acid groups such as sulfonic and phosphonic providing high conductivities and the relatively weak acid groups such as carboxylic and phenolic providing low conductivities.

Examples of polymeric electronic humidity sensors are given in U.S. Pat. No. 2,728,831 to Pope and U.S. Pat. No. 2,937,524 to Gregor. The sensors of these patents are hydrocarbon (e.g., polystyrene) based with sulfonic acid being a preferred functional group.

Other examples of organic polymers proposed for electronic humidity sensing include polyphenylacetylene (Hermans, "CO, $CO_2$, $CH_4$ and $H_2O$ Sensing by Polymer Covered Interdigitated Electrode Structures," *Sensors and Actuators*, Vol. 5, pp. 181-186, 1984); cellulose acetate (Delapierre et al, "Polymer-Based Capacitive Humidity Sensor: Characteristics and Experimental Results," *Sensors and Actuators*, Vol. 4, pp. 97-104, 1983); and cellulose acetate butyrate (Misevich, "Capacitive Humidity Transducers," *IEEE Trans. Ind. Electron. Conf. Instrum.*, pp. 6-12, 1969; Thoma et al, "A Capacitance Humidity-Sensing Transducer," *IEEE Trans. Com. Hybrids Manuf. Tech.*, pp. 321-323, 1979). Notably, for reasons which will become apparent later, all of the foregoing polymers are hydrocarbons.

In spite of the variety of polymers available and the many improvements accomplished in recent years, state-of-the-art polymeric humidity sensors still suffer from a variety of significant disadvantages including hysteresis, non-linearity, instability, and lack of selectivity—all of which contribute to poor accuracy. State-of-the-art sensors are further limited in that they are generally characterized by short service life. Other problems associated with known organic polymer sensors include swelling and oxidation. Most significantly, these disadvantages become increasingly severe at elevated temperatures and high levels of relative humidity. Such temperature and humidity conditions frequently prevail in manufacturing environments, for example, in which humidity control may be required. An environment of this type might be the interior of a microwave oven or an industrial drier. Because of their disadvantages, polymeric humidity sensors have generally had little or no utility in such environments. Metal oxide (ceramic) humidity sensors exhibit similar disadvantages and have likewise been of only limited utility.

During the course of development of the present invention, many polymers were examined in an effort to produce a sensor which would provide high accuracy measurements with a long service life in high temperature-humidity conditions. In U.S. Pat. No. 4,083,765 to Lawson, an electrolytic hygrometer was disclosed incorporating a polymer sensing element having a long service life without exhibiting major performance deterioration. In particular, Lawson used a sensing element of perfluorocarbon polymer having pendant sulfonic acid groups. The element was of a tubular configuration with a pair of electrodes in contact with the inner and outer walls of the tube. A DC current through the element was measured as absorbed water was electrolyzed to hydrogen and oxygen to provide an indication of the water content of a test gas. Lawson did not consider use of the aforementioned polymer in an electronic thin-film humidity sensor. Developmental work in connection with the present invention, however, revealed that in such applications, this polymer is sensitive to variations in relative humidity only up to about 40 percent, with little change in response as humidity increases further. Thus, despite its improved service life, the polymer employed by Lawson, like others proposed heretofore, proved to be of little practical value for electronic humidity sensing applications in high temperature-humidity environments.

SUMMARY OF THE INVENTION

It has been discovered in accordance with the present invention that the limitations of known organic polymer humidity sensors in high temperature-humidity applications may be overcome through the use of halogenated organic polymers having pendant thereto both groups of a relatively strong acidic type and groups of a relatively weak acidic type. As will be described in some detail hereinafter, the combined advantages of halogen in the polymer and the presence of two pendant functional groups as aforesaid provides for long sensor life and lasting accuracy. Furthermore, as will also be discussed, the use of such polymers admits not only of electronic humidity sensing applications but of acoustic and optical humidity sensing applications as well.

More particularly stated, in one of its aspects, the invention provides humidity sensitive apparatus comprising a thin film of hygroscopic, halogenated organic polymer having pendant groups of a relatively strong acidic type and pendant groups of a relatively weak acidic type, and means attached to the polymer film for applying to the same a signal of a type having a parameter which will be affected by the polymer film in varying degree as a function of the water content of said polymer film.

According to preferred practice of the invention, the polymer may be a perfluorocarbon polymer or a perchlorinated polymer, with the former being the more preferred—an example being perfluoroethylene. The pendant groups are preferably carboxylic and sulfonic acid groups, most advantageously present with a ratio in the range of about 1:100 to about 100:1. Particularly in the case of electronic humidity sensing applications, a ratio of carboxylic to sulfonic acid groups from about 1:2 to about 1.5:1 may often offer the best performance characteristics, due to good polymer conductivity with low hysteresis.

Other aspects of the invention relate to methods of making humidity sensitive apparatus of the type just described, as well as humidity measuring methods and apparatus incorporating such humidity sensitive apparatus. These additional aspects of the invention, along with those previously described, will be more fully appreciated from the ensuing detailed description of the invention, as will the invention's many advantages.

BRIEF DESCRIPTION OF THE DRAWINGS

The invention will be best understood when the description is considered in conjunction with the accompanying drawing, wherein.

DETAILED DESCRIPTION OF THE INVENTION

Figure 1:
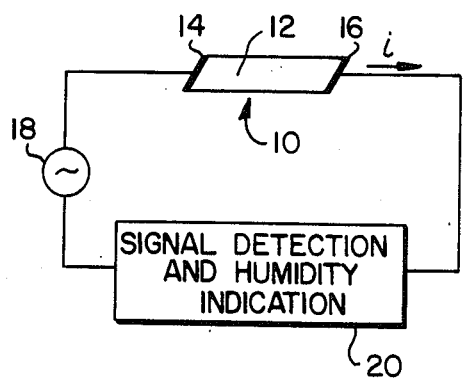
FIG. 1 is a diagram of an electronic humidity measurement system incorporating a humidity sensitive element in accordance with the invention.
Figure 2:
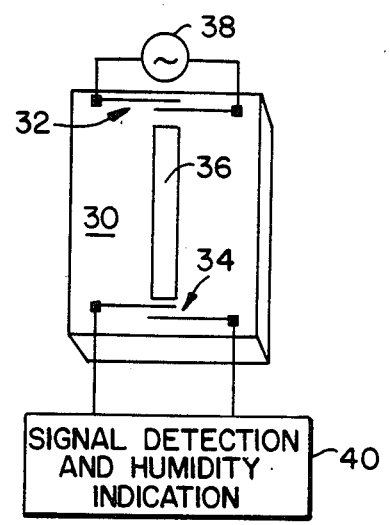
FIG. 2 is a diagram of a system for acoustic humidity measurement in accordance with the invention.
Figure 3:
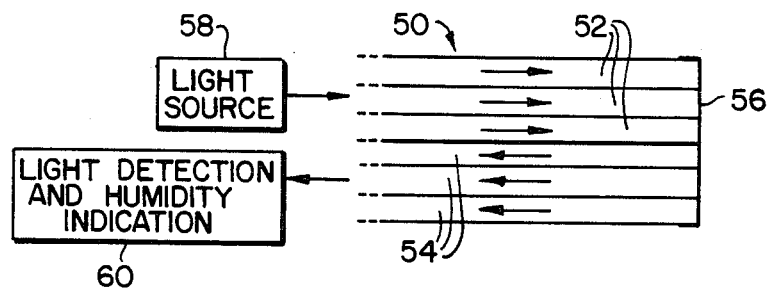
FIG. 3 is a diagram of another system in accordance with the invention for optical humidity measurement.

FIGS. 1-3 illustrate several systems for measuring relative humidity in accordance with the present invention. As will be described in more detail later, the systems are respectively adapted to measure humidity electronically, acoustically, and optically. More particularly, as will be described in more detail later, the systems are adapted respectively to apply electrical, acoustic and optical signals to a polymer, the signals each having a parameter, the value of which will be established by the water content of the polymer (which is, in turn, a function of ambient relative humidity at a given temperature). In each system, a humidity sensitive element including a thin film or membrane of hygroscopic organic polymer is employed for sensing the water content of the ambient environment which may, for example, be the interior of an industrial microwave oven or other industrial drying apparatus in which the polymer film may be exposed to temperatures on the order of 50°-100° C. or more and relative humidities typically from about 30% up to 100%.

While the use of organic polymers as humidity sensing elements is well-known, as discussed earlier herein, the polymers employed in the present invention are marked by two distinguishing characteristics. First, is the presence of a halogen in place of hydrogen, and second is the presence of two types of pendant functional group—in particular, a relatively strong acidic group such as the sulfonic acid group ($SO_3H$) or the phosphonic acid group ($PO_3H$) and a relatively weak acidic group such as the carboxylic acid group (COOH) or the phenolic acid group ($C_6H_5OH$). Among the halogens, fluorine and chlorine are preferred for the practice of the invention, with fluorine being the most preferred.

Halogenated polymer membranes (polyelectrolyte membranes) with pendant strong and weak acidic groups are known per se and are available commercially, although no known attempt has been made heretofore to incorporate such membranes into humidity sensing apparatus. Fluorinated membranes, for example, having both pendant carboxylic acid groups and pendant sulfonic acid groups may be prepared in accordance with the techniques described in U.S. Pat. No. 4,357,218 to Seko, incorporated herein by reference. An exemplary polymer of this type is shown structurally below and includes a linear perfluoroethylene backbone with the acid groups pendant from the side chains. The membrane may be obtained commerically from DuPont de Nemours Co. under the trade designation NAFION, and will be referred to by way of example in explaining the invention hereinafter.

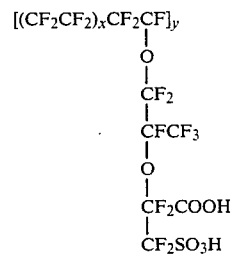

By using techniques similar to those described in Seko, other halogenated polymer membranes with pendant sulfonic and carboxylic acid groups may be formed. For example, if chlorine is the desired halogen for a particular application, a copolymer of styrenesulfonate with polyvinylchloride may be molded into a membrane and then impregnated by suitable techniques (e.g., dipping) with a solution of acrylic acid to form the acid groups. Techniques for incorporating other acidic groups such as phosphonic and phenolic acid groups into halogenated polymers are within the level of ordinary skill in the polyelectrolyte art. The preparation of polymer membranes for use in humidity sensing apparatus does not constitute part of the present invention and will therefore not be addressed further.

Without any intention of limiting the invention by theory, the use of membranes in which hydrogen has been substituted by halogen and in which pendant groups of both a relatively strong acidic type and a relatively weak acidic type are present is based upon two respective considerations. Regarding the presence of halogen, the tendency of a polymer membrane to swell on adsorption of water vapor and the general stability (e.g., resistance to oxidation) of the polymer at high temperature-humidity conditions is believed to be substantially related to the basic molecular structure of the particular polymer. More specifically, it appears that the tighter the molecular structure of the polymer, the more hydrophobic and resistant to swelling it will be, as well as more generally stable. Halogens, in particular, fluorine and chlorine, have two especially significant characteristics in comparison with hydrogen in this respect. First, fluorine and chlorine both have substantially smaller ionic radii than hydrogen (1.36 and 1.81 angstroms, respectively, vs. 2.08 angstroms for hydrogen). Second, both are capable of forming strong bonds in the polymer backbone, the fluorine bonds generally being considerably stronger than the bonds formed by hydrogen. The small ionic radii and high bonding strength of fluorine and chlorine result in compact, tightly bound molecular structures having the aforementioned advantages. Halogenated polymers will also be of considerably higher molecular weight than hydrocarbons, a factor which may also contribute to better stability.

While fluorine and chlorine are preferred among the halogens for practicing the invention, certain advantages of the invention may be obtained with polymers containing other halogens, such as bromine, and it is within the broader aspects of the invention to utilize such materials. As between fluorine and chlorine, it will be appreciated that fluorine is highly preferred due to its smaller ionic radius and capability of forming much stronger bonds.

Naturally, molecular structures will be tightest when all hydrogen in the polymer backbone has been substituted with halogen, although it is consistent with the invention to employ partially substituted polymers having the pendant acidic groups attached thereto. Hence, perfluorinated and perchlorinated polymers are especially preferred for the practice of the invention. Perfluorinated membranes, for example, exhibit particularly superior resistance to chemical corrosion and maintain excellent thermal stability up to 150° C.

The use of two types of pendant acidic group, one a relatively strong acidic group and one a relatively weak acidic group, is principally directed to the problem of hysteresis. Hysteresis is manifested by a lack of consistency in the response of a sensor to identical conditions occurring at different times. For example, a sensor may indicate a particular relative humidity, say 30%, at one point in time given a fixed set of conditions (temperature and ambient water vapor pressure), and thereafter, when the same conditions reoccur at a time after exposure of the sensor to various temperature-humidty conditions, the same sensor may indicate a different relative humidity, say 31%—a three percent difference from the previous reading. Sensor error due to hysteresis may vary unpredictably over time as the conditions to which the sensor is subjected may likewise vary. Thus, if a sensor having such characteristics is to be of practical value, frequent recalibrations are required.

It is believed that the phenomenon of hysteresis is largely due to the tendency of adsorbed water molecules to form hydrogen bonds within the polymer matrix—in particular, hydrogen bonds with the functional groups attached to the polymer backbone. By this mechanism, the water molecules become bonded within the polymer matrix so that when humidity decreases, a certain number of these molecules will remain bonded within the polymer rather than being desorbed. Because the water molecules are retained in the polymer, the basic sensor characteristics are altered, causing hysteresis error as previously described.

Accordingly, it is theorized that to minimize hysteresis, in thermodynamic equilibrium the chemical potential of water molecules within the polymer must be kept to a minimum at a given temperature and relative humidity. That is, the entropy of adsorption/desorption of water molecules on the polymer must be kept to a maximum. The use of polymers having relatively strong and relatively weak pendant acidic groups in accordance with the invention is based on this principle. More particularly, the weaker acidic groups appear to have a much lower tendency than the stronger acidic groups to form hydrogen bonds with adsorbed water. The weak acidic groups thus perform the function of limiting the population of hydrogen-bonded water molecules retained in the polymer, thus controlling the hydrophilic character of the polymer. By minimizing the number of hydrogen-bonded water molecules retained in the polymer, hysteresis is also kept to a minimum.

Among the various acid groups mentioned earlier herein, it is highly preferred to employ sulfonic acid groups together with carboxylic acid groups, as these are respectively the strongest and weakest of these acids and provide high selectivity to water vapor with excellent hysteresis. For electronic applications, the high conductivity offered by the strong sulfonic groups is also a significant advantage.

Generally speaking, the carboxylic and sulfonic acid groups are most advantageously present in a ratio (carboxylic-to-sulfonic) from about 1:100 to about 100:1. Polymers having acid group ratios within this range offer a number of significant advantages, including high resistance to oxidation, high selectivity to water vapor, high electrical conductivity, long service life and exceptional durability. This is especially true for perfluorinated polymers. It will be appreciated in regard to electronic sensors that the selected acid group ratio in any given application will involve a balance between conductivity and hysteresis. The greater the proportion of sulfonic acid groups present, the greater will be the conductivity, but also the greater the hysteresis due to the lower proportion of carboxylic acid groups. An acid group ratio in the range of about 1:2 to about 1.5:1 should provide acceptable conductivity and hysteresis for most high temperature-humidity applications. A ratio of about 1:1 has been found to provide particularly good sensor characteristics in terms of conductivity, sensitivity, and hysteresis, as will be seen shortly. (The foregoing reasoning is similarly applicable in selecting ratios between different combinations of acid groups.)

Having described the polymers used in the practice of the present invention, it is now appropriate to consider several humidity sensitive devices incorporating these polymers. Referring again to the drawing, FIG. 1 illustrates electronic humidity measurement apparatus in accordance with the invention. In FIG. 1, a humidity sensor 10 comprises a thin polymer film 12 formed of a polymer of the type described hereinabove, and electrodes 14 and 16 attached to the polymer film 12 at spaced locations, as shown. The electrodes may conveniently be formed of metallic paint, as is well known in the art. An appropriate voltage source 18 is connected between the electrodes to apply a voltage therebetween. The voltage may be DC, but is preferably AC with a frequency of at least about 10 kilohertz to avoid possible interference with the electrical signal passed by the polymer due to any small gaps between the electrodes and polymer film and/or space-charge polarization at grain boundaries. The current flow i through the polymer film as a result of the applied voltage will vary as a function of the water content of the film and, therefore, relative humidity (at any given temperature). The current i may be detected and a humidity indication provided, based on conductivity or resistance corresponding to the current flow, by suitable apparatus 20, as is well known in the art.

Figure 4:
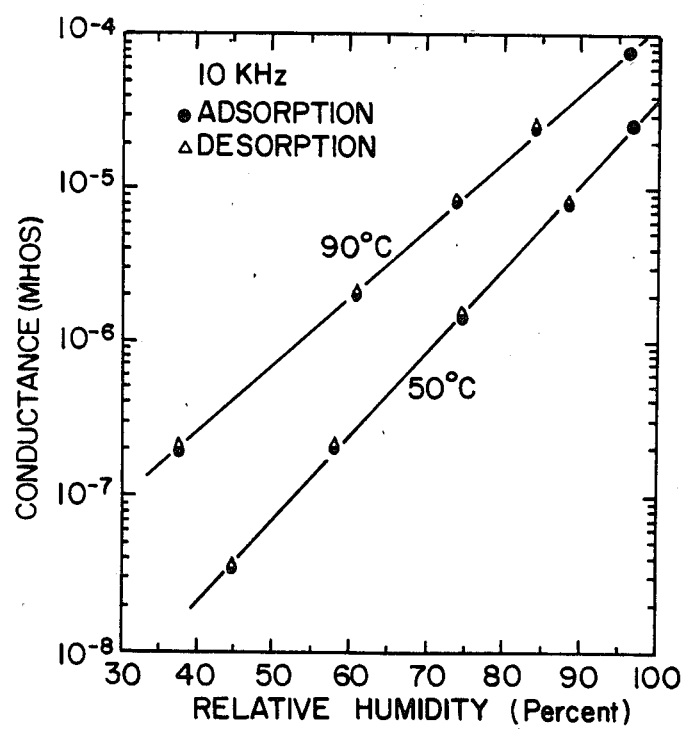
FIG. 4 is a graph of performance data obtained from a system of the type shown in FIG. 1.

FIG. 4 shows test data obtained from humidity sensing apparatus of the type shown in FIG. 1. For test purposes, a NAFION membrane of the type previously described was employed (in particular, perfluoroethylene having pendant carboxylic and sulfonic acid groups). The acid group ratio was about 1:1, and the membrane had dimensions of 12 mm by 3 mm, with a thickness of 0.1 mm. To prepare it for use as a humidity sensor, the polymer film was cleaned in boiling trichloroethylene for 10 minutes, followed by boiling in distilled water for 30 minutes. The film was then cooled to room temperature in the distilled water bath, whereupon it was removed and air-dried. A conductive silver paint was applied to the ends of the polymer film element to form the electrodes.

The test procedure involved placing the completed element over saturated salt solutions of potassium nitrite ($KNO_2$), sodium nitrite ($NaNO_2$), sodium nitrate ($NaNO_3$), sodium chloride (NaCl), and barium chloride ($BaCl_2$), and sodium fluoride (NaF), at temperatures of 50° and 90° C. to provide relative humidities between approximately 38% and 97%. Conductivity of the polymer membrane was then determined as a function of relative humidity. (At lower temperature-humidity conditions, conductivity is lower and may not be as conveniently measured as with the present test conditions, although the invention is nonetheless applicable under such circumstances.) Estimated maximum errors in relative humidity values generated by these solutions over the specified temperature range are less than 1% in all cases. The applied voltage had a frequency of 10 kilohertz with current flow through the polymer film being less than 1 microampere. The element was subjected to four adsorption-desorption cycles over the aforementioned range of relative humidities. Each data point shown in FIG. 4 represents an average value for the four humidity cycles.

Results indicate that the sensing element described is linear to within 1% relative humidity and exhibits hysteresis of less than 1% relative humidity. The sensor is also extremely stable and has a precision of better than 1% relative humidity. Notably, the sensitivity of the element (change in conductivity versus change in relative humidity) in the test temperature-humidity range covers three orders of magnitude, which is at least one order of magnitude higher than sensors heretofore proposed, including metal oxide (ceramic) sensors. It is thus apparent that humidity sensitive devices made in accordance with the invention are extremely well suited to the severe conditions which may be experienced in industrial driers, microwave ovens and the like.

Turning now to FIG. 2, another type of humidity sensitive device in accordance with the invention is shown. In particular, the illustrated device employs a surface acoustic wave-type humidity sensor. Basic principles and considerations in connection with the use and design of acoustic vapor sensing devices are discussed in Wohltjen, "Mechanism of Operation and Design Considerations for Surface Acoustic Wave Device Vapour Sensors," *Sensors and Actuators,* Vol. 5, 1984, pp. 307–325. The particular device herein illustrated utilizes a surface acoustic wave guide of the basic type described in my co-patent U.S. Pat. No. 4,330,768 (incorporated herein by reference). Basically, the wave guide comprises a block of piezoelectric material 30, such as lithium tantalate, capable of propagating a surface acoustic wave. A pair of suitable transducers 32 and 34 ar respectively disposed at opposite ends of the body for generating and receiving the surface acoustic wave along the top surface of the body. Transducer 32 is connected to an appropriate energy source 38, while transducer 34 is connected to suitable signal detection and humidity indicating means 40, as shown. In accordance with the invention, a wave guide region 36 of the piezoelectric body may be covered with a thin film of polymer of the previously described type for interaction with the acoustic wave traveling from transducer 32 to transducer 34. As ambient humidity conditions change, the mass of the polymer film on region 36 will vary so that the velocity of the acoustic wave will likewise vary due to interaction of the wave with the polymer film. The actual velocity of the surface acoustic wave may be determined by detecting the phase shift of the wave and will be indicative of relative humidity conditions at a given temperature.

If desired, the foregoing structure may be varied by leaving wave guide region 36 uncovered and covering the remainder of the top surface of body 30 with a polymer film. Confinement of the acoustic energy to the wave guide region may be ensured by diffusing metals appropriately into body 30 to regulate the relative speeds of sound in the wave guide and surrounding regions in accordance with known techniques.

Another possible modification would be to incorporate a metallic film overlay on the wave guide region surface, as described in my aforementioned co-patent, to eliminate acoustic dispersion. In the case of apparatus wherein the wave guide region is provided with a polymer film cover, the metallic overlay would be placed over and bonded to the polymer film and would be made porous to permit adsorption and desorption of water vapor from the ambient environment by the polymer film.

FIG. 3 shows a third embodiment of humidity sensitive apparatus in accordance with the invention—in this case, an optical device. In the form shown, the humidity sensitive element includes a fiberoptic bundle 50, composed of light transmitting optical fibers 52 and light receiving optical fibers 54, with a polymer film 56 of the previously described type attached to one end of the bundle 50, as shown. Attachment of the membrane to the bundle may be accomplished, for example, by dipping the bundle into the polymer in liquid state and then spinning the bundle to obtain the desired film coating. A light source 58, which may be a light emitting diode, emits light into the transmitting fibers 52, and a portion of the light impinging film 56 will be scattered thereby and received by fibers 54 in an amount depending on the water content of the film. The received light may directed through the fibers to appropriate light detecting and humidity indicating means 60, as shown.

While th invention and several embodiments for its practice have been described herein, it will be apparent to those skilled in the art that changes and modifications may be made which are within the principles and spirit of the invention, the scope of which is defined in the appended claims. For instance, it will be apparent that the pendant functional groups need not be acid groups per se, but may be groups of acidic salts. Examples of such salts include potassium and sodium salts of those acid groups mentioned earlier herein (e.g., $SO_3Na$, $PO_3Na$ and $CO_2K$). Thus, hereinafter in the claims, references to acidic groups are intended to include groups of both acids and salts although the acid groups are more preferred in the practice of the invention.

I claim:

1. Humidity sensitive apparatus comprising a thin film of hygroscopic, halogenated organic polymer having pendant groups of a relatively strong acidic type and pendant groups of a relatively weak acidic type, and means attached to said polymer film for applying to the same a signal of a type having a parameter which will be affected by said polymer film in varying degree as a function of the water content of said polymer film.

2. Apparatus in accordance with claim 1, wherein said hygroscopic halogenated organic polymer is selected from the group consisting of fluorinated polymers and chlorinated polymers.

3. Apparatus in accordance with claim 2, wherein said relatively strong acidic groups are selected from sulfonic groups and phosphonic groups and wherein said relatively weak acidic groups ar selected from carboxylic groups and phenolic groups.

4. Apparatus in accordance with claim 3, wherein said hygroscopic halogenated organic polymer is selected from the group consisting of perfluorinated polymers and perchlorinated polymers.

5. Apparatus in accordance with claim 4, wherein said signal applying means comprises means for subjecting said polymer film to an optical signal.

6. Apparatus in accordance with claim 5, wherein said signal applying means comprises a fiberoptic bundle having said polymer film attached to an end thereof.

7. Apparatus in accordance with claim 4, wherein said signal applying means comprises means for subjecting said polymer to an acoustic signal.

8. Apparatus in accordance with claim 7, wherein said signal applying means comprises a piezoelectric body having acoustic transducer means attached thereto for generating a surface acoustic wave on a surface of said body, said polymer film being attached to said surface in a position for interaction with said surface acoustic wave.

9. Apparatus in accordance with claim 4, wherein said signal applying means comprises means for applying an electrical signal to said polymer film.

10. Apparatus in accordance with claim 9, wherein said signal applying means comprises a pair of electrodes attached to said polymer film at spaced apart locations in electrical contact therewith.

11. Apparatus in accordance with claim 9, wherein said signal applying means comprises means for subjecting said polymer film to an alternating current having a frequency of at least about 10 kilohertz.

12. Apparatus in accordance with claim 4, wherein said pendant groups are carboxylic acid groups and sulfonic acid groups and wherein the ratio of said carboxylic acid groups to said sulfonic acid groups is within the range of about 1:100 to about 100:1.

13. Apparatus in accordance with claim 12, wherein said organic polymer is perfluoroethylene.

14. Apparatus in accordance with claim 12, wherein the ratio of said carboxylic acid groups to said sulfonic acid groups with within the range of about 1:2 to about 1.5:1.

15. A system for measuring humidity comprising humidity sensitive apparatus in accordance with claim 12, means connected to said polymer film for detecting said parameter of said signal, and means for providing an indication of relative humidity based on said detected parameter.

16. A method of constructing humidity sensitive apparatus, comprising providing a thin film of hygroscopic, halogenated organic polymer having pendant groups of a relatively strong acidic type and pendant groups of a relatively weak acidic type and attaching to said polymer film means for applying to the same a signal of a type having a parameter which will be affected by said polymer film in varying degree as a function of the water content of said polymer film.

17. A method in accordance with claim 16, wherein said hygroscopic, halogenated organic polymer is selected from the group consisting of fluorinated polymers and chlorinated polymers.

18. A method in accordance with claim 17, wherein said relatively strong acidic groups are selected from sulfonic groups and phosphonic groups and wherein said relatively weak acidic groups are selected from carboxylic groups and phenolic groups.

19. A method in accordance with claim 18, wherein said hygroscopic, halogenated organic polymer is selected from the group consisting of perfluorinated polymers and perchlorinated polymers.

20. A method in accordance with claim 19, wherein said signal applying means comprises means for applying an optical signal to aid polymer film.

21. A method in accordance with claim 20, wherein said signal applying means comprises optical fiber means for directing a beam of light at said polymer film for interaction therewith and optical fiber means for receiving a portion of said light beam following said interaction.

22. A method in accordance with claim 19, wherein said signal applying means comprises means for subjecting said polymer film to an acoustic signal.

23. A methdd in accordance with claim 22, wherein said signal applying means comprises a surface of a piezoelectric body attached to said polymer film, said body having acoustic transducer means for generating a surface acoustic wave for interaction with said polymer film.

24. A method in accordance with claim 19, wherein said pendant groups are carboxylic acid groups and sulfonic acid groups, with the ratio of said carboxylic acid groups to said sulfonic acid groups being in the range of about 1:100 to about 100:1.

25. A method in accordance with claim 24, wherein said ratio is in the range of about 1:2 to about 1.5:1.

26. A method in accordance with claim 24, wherein said hygroscopic, halogenated organic polymer is perfluoroethylene.

27. A method in accordance wit claim 19, wherein said signal applying means comprises means for applying an electrical signal to said polymer film.

28. A method in accordance with claim 27, wherein said signla applying means comprises a pair of electrodes at spaced apart locations on said polymer film, in electrical contact therewith.

29. A method in accordance with claim 28, wherein said signal applying means comprises means for connecting said electrodes to an alternating electrical voltage with a frequency of at least about 10 kilohertz.

30. A method for measuring humidity comprising providing humidity sensitive apparatus in accordance with claim 16, applying said signal to said polymer film, detecting said parameter of said signal, and providing an indication of relative humidity based on said detected parameter.

* * * * *